US00PP31997P2

(12) United States Plant Patent

Van Huylenbroeck et al.

(10) Patent No.: US PP31,997 P2
(45) Date of Patent: Jul. 21, 2020

(54) *HYDRANGEA* PLANT NAMED 'ILVOCLOU'

(50) Latin Name: *Hydrangea macrophylla*
Varietal Denomination: ILVOCLOU

(71) Applicants: Johan Van Huylenbroeck, Melle (BE); Katrijn Van Laere, Melle (BE)

(72) Inventors: Johan Van Huylenbroeck, Melle (BE); Katrijn Van Laere, Melle (BE)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 16/501,703

(22) Filed: May 23, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

(56) References Cited

PUBLICATIONS

UPOV hit on *Hydrangea* plant named 'ILVOCLOU', QZ PBR 20182288, application date Dec. 16, 2018.*

* cited by examiner

*Primary Examiner* — Anne Marie Grunberg
(74) *Attorney, Agent, or Firm* — Cassandra Bright

(57) ABSTRACT

A new and distinct *Hydrangea* plant named 'ILVOCLOU' is disclosed, characterized by compact plants producing lace-cap inflorescences having light violet-blue sterile flowers with purple sepals and medium violet-blue fertile flowers. Plants produce attractive foliage and bloom abundantly. The new variety is a *Hydrangea*, normally produced as an ornamental plant.

2 Drawing Sheets

Figure 1:
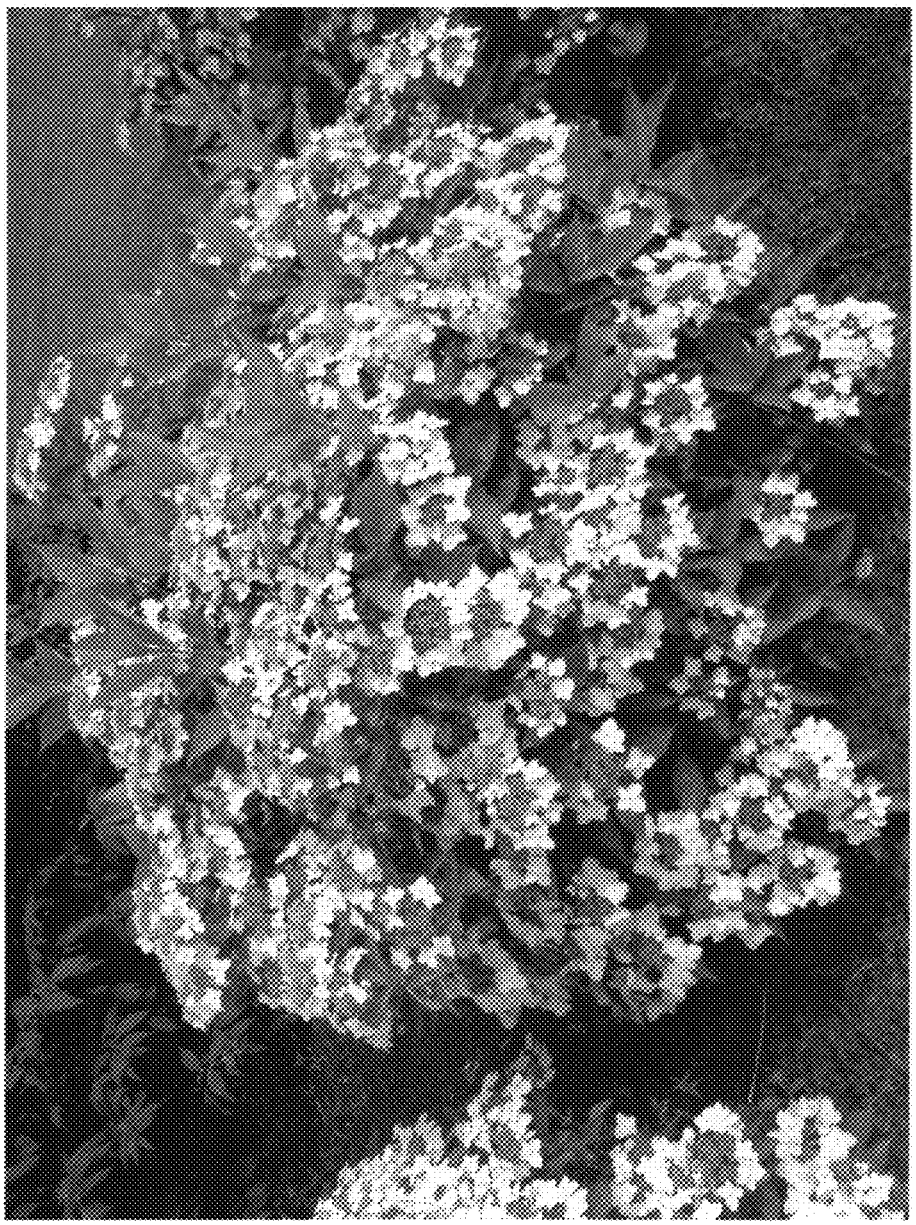

Latin name of the genus and species: *Hydrangea macrophylla.*

Variety denomination: 'ILVOCLOU'.

BACKGROUND OF THE INVENTION

The new *Hydrangea* cultivar is a product of a planned breeding program conducted by the inventors, at a commercial nursery in Melle, Belgium. The objective of the breeding program was to produce new *Hydrangea* varieties with compact habits and strong blooming beginning in the first year. The cross resulting in this new variety was made during Summer of 2003.

The seed parent is the unpatented variety *Hydrangea serrata* 'Bluebird'. The pollen parent is the unpatented variety *Hydrangea macrophylla* 'Mariesii Perfecta'. The new variety was identified as a potentially interesting selection in the Summer of 2007, at a commercial greenhouse in Melle, Belgium.

Asexual reproduction of the new cultivar 'ILVOCLOU' by vegetative soft wood cuttings was first performed during the Summer of 2016, at a commercial greenhouse in Melle, Belgium. Subsequent propagation has shown that the unique features of this cultivar are stable and reproduced true to type in 6 successive generations.

SUMMARY OF THE INVENTION

The cultivar 'ILVOCLOU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ILVOCLOU' These characteristics in combination distinguish 'ILVOCLOU' as a new and distinct *Hydrangea* cultivar:

1. Compact plants.
2. Lace-cap inflorescence.
3. Sterile flowers colored light violet blue-with purple sepals.
4. Fertile flower colors colored medium violet-blue.
5. Abundant flowering.
6. Attractive foliage.

PARENT COMPARISON

Plants of the new cultivar 'ILVOCLOU' are similar to plants of the seed parent variety *Hydrangea serrata* 'Bluebird' in most horticultural characteristics, however, plants of the new cultivar 'ILVOCLOU' differ in the following;

1. The new variety has more showy sepals than the seed parent.
2. The new variety is a more compact plant than the seed parent.

Plants of the new cultivar 'ILVOCLOU' are similar to plants of the pollen parent variety *Hydrangea macrophylla* 'Mariesii Perfecta' in most horticultural characteristics, however, plants of the new cultivar 'ILVOCLOU' differ in the following;

1. The new variety has lighter green foliage than the pollen parent variety.

2. The new variety has more showy sepals than the pollen parent.
3. The new variety has a stronger flower color than the pollen parent.

COMMERCIAL COMPARISON

Plants of the new cultivar 'ILVOCLOU' can be compared to the variety *Hydrangea macrophylla* 'SMHMLDD', U.S. Plant Pat. No. 25,105. These varieties are similar in most horticultural characteristics; however 'ILVOCLOU' differs in the following:

1. The new variety has lighter green foliage than this comparator.
2. The new variety is more floriferous than this comparator.
3. The new variety is a more compact plant than this comparator.

BRIEF DESCRIPTION OF THE PHOTOGRAPHS

The accompanying photograph in FIG. 1 illustrates in full color a typical plant of 'ILVOCLOU'.

Figure 2:
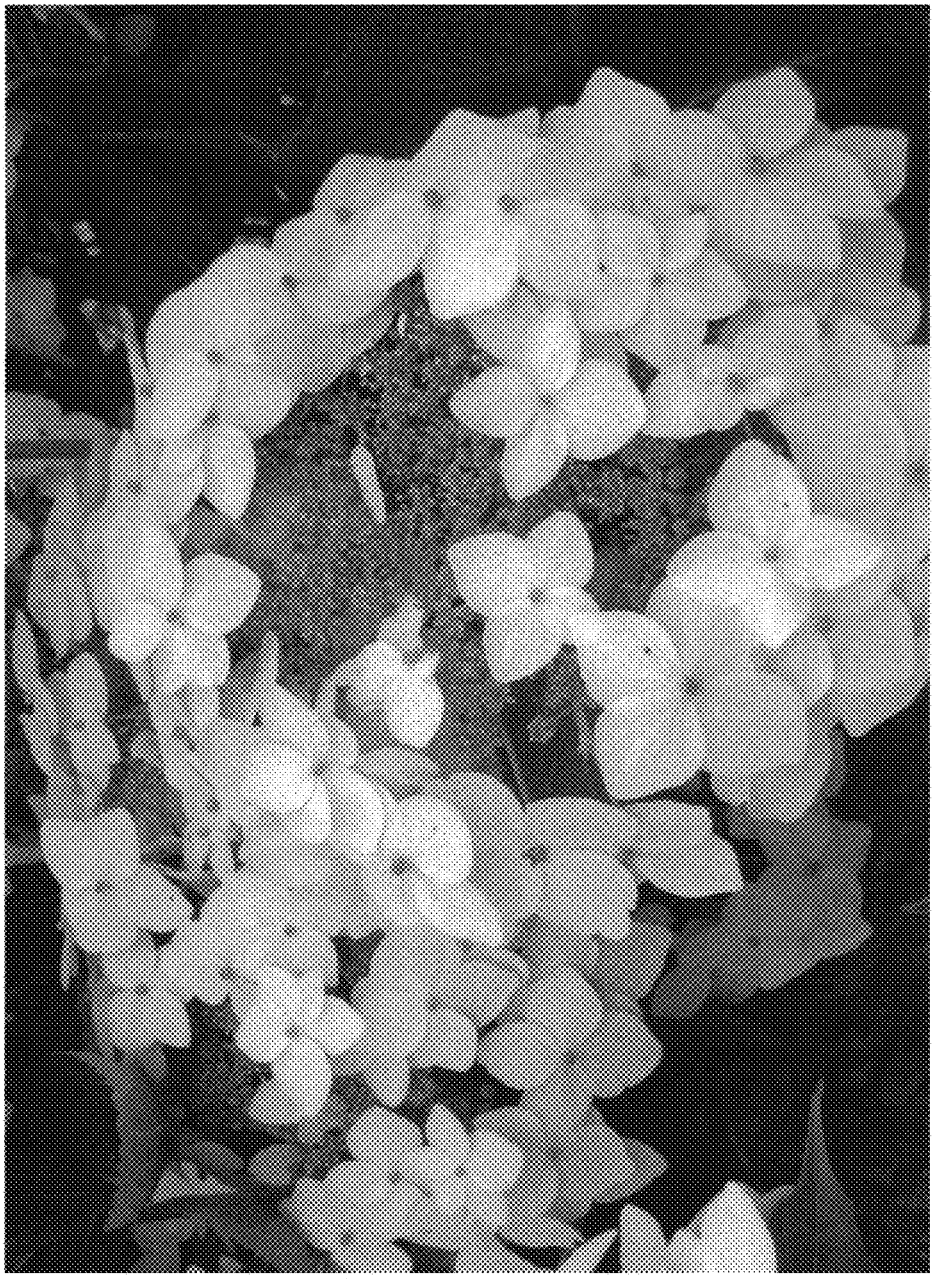

FIG. 2 illustrates in full color a typical inflorescence of 'ILVOCLOU' grown in an outdoor flower bed, in Grand Haven, Mich. Age of the plant photographed is approximately 4 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'ILVOCLOU' plants grown in a commercial poly greenhouse in Grand Haven, Mich. under natural lighting. Measurements were taken during the July of 2015. The plants were about 4 years old planted in the ground. The growing temperature ranged from 5° C. to 27° C. Measurements and numerical values represent averages of typical plant types.

Botanical classification: *Hydrangea macrophylla* 'ILVOCLOU'.

PROPAGATION

Time to initiate roots: Approximately 18 days at approximately 27° C.

Time to produce a rooted young plants: Approximately 60 days at approximately 27° C.

Root description: Fibrous. Free to moderately free root branching, fine roots. Roots mainly white, about RHS White 155D.

Propagation method: Softwood cuttings.

PLANT

Plant type: Flowering deciduous perennial shrub.

Age of plant described: Approximately 4 years old.

Growth habit: Mound.

Overall plant shape: Upright and mounded.

Height: 80 to 100 cm.

Plant spread: 60 to 80 cm.

Growth rate: Good.

Plant vigor: Moderate.

Branching characteristics:

Length of primary lateral branches: Up to 80 cm.

Diameter of lateral branches: 5 to 7 mm.

Quantity of lateral branches: 8 to 10.

Stem:

*Stem shape.*—Round.

*Stem strength.*—Strong.

*Color.*—Immature: Near RHS Yellow-Green 144B and 145B. Mature: Turning in Fall to RHS Red 53B.

*Pubescence.*—None, glabrous.

*Aspect.*—Upright and outwards.

Internode length: 6 to 10 cm.

FOLIAGE

Leaf:

*Arrangement.*—Opposite, simple.

*Leaf shape.*—Lanceolate to ovate.

*Average length.*—13.8 cm.

*Average width.*—7.6 cm.

*Apex.*—Acuminate.

*Base.*—Acute to obtuse.

*Margin.*—Serrate.

*Texture of top surface.*—Glabrous, slightly rugose.

*Texture of bottom surface.*—Glabrous.

*Leaf pubescence.*—None.

*Color.*—Young foliage upper side: Near RHS Yellow-Green 144A. Young foliage under side: Near RHS Yellow-Green 144D. Mature foliage upper side: Near RHS Yellow-Green 144A. Mature foliage under side: Near RHS Yellow-Green 144C. Fall foliage upper wide: Near RHS Greyed-Purple 183A and 187A. Fall foliage under side: Near RHS Green 139C.

*Venation.*—Pattern: Cross-venulate, reticulate. Color upper side: Near RHS Yellow-Green 144A. Color under side: Near RHS Yellow-Green 144D.

*Petiole.*—Average Length: 3.2 cm. Diameter: 0.28 cm. Petiole color upper side: Near RHS Yellow-Green 145C. In Fall speckled Greyed-Red 178A. Petiole color lower side: Near RHS Yellow-Green 145C. Petiole Texture upper side: Smooth, glabrous. Petiole Texture lower side: Smooth, glabrous.

FLOWER

Natural flowering season: June, July and August. Plants flower during the first year of production.

Inflorescence:

*Type.*—Lace-cap composed of single sterile and fertile flowers.

*Quantity of flowers per inflorescence.*—Fertile flowers.—49. Sterile Flowers: Average 11.

*Persistent or self-cleaning.*—Persistent.

*Fragrance.*—None detected.

Panicle:

*Shape.*—Flattened globular.

*Height.*—5 cm.

*Diameter.*—10 cm.

Sterile flower:
*Bud shape*.—Flattened globular.
*Bud length*.—3 mm.
*Bud diameter*.—3 mm.
*Bud color*.—Near RHS Violet-Blue 91A and Purple 75A.
*Flower aspect*.—Upright and outward.
*Flower shape*.—Rotate.
*Flower length*.—Average range 3-4 cm.
*Flower diameter*.—*Average range* 3-4 cm.
*Flower depth*.—0.9 cm.
*Persistence*.—Persistent.
*Longevity on plant*.—3 to 4 months.

Sterile flower petals:
*Petal arrangement*.—Single whorl.
*Quantity*.—4.
*Length of petal*.—3.2 mm.
*Width of petal*.—2.8 mm.
*Apex*.—Acute.
*Shape of petal*.—Obovate.
*Petal margin*.—Entire.
*Petal base*.—Truncate.
*Petal texture*.—Smooth, glabrous, upper and under side.
*Color*.—Upper surface at first opening: Near RHS Violet-Blue 92D. Under surface at first opening: Near RHS Violet-Blue 92D. Upper surface at maturity: Near RHS Violet-Blue 95B. Under surface at maturity: Near RHS Violet-Blue 95B.

Sterile flower sepal:
*Arrangement*.—Single whorl.
*Number*.—4, or occasionally 5.
*Shape*.—Ovate.
*Tip*.—Acute.
*Base*.—Cuneate.
*Margin*.—Entire.
*Length*.—Average 2 cm.
*Width*.—Average 1.5 cm.
*Texture, upper*.—Smooth, glabrous.
*Texture, lower*.—Smooth, glabrous.
*Color*.—Upper surface at first opening: Near RHS Yellow-White 158B. Under surface at first opening: Near RHS Yellow-White 158B. Upper surface at maturity: Near RHS Purple 76B and 76C, colors flushed together. Under surface at maturity: Near RHS Purple 76B and 76C, colors flushed together. Fading to Upper surface: In Fall persistent sterile sepals turn RHS Yellow-Green 145B flushed Greyed-Red 180A. Fading to Under surface: In Fall persistent sterile sepals turn RHS Yellow-Green 145B flushed Greyed-Red 180A.

Sterile flower pedicel:
*Length*.—Average 3.0 cm.
*Diameter*.—1 to 1.5 mm.
*Angle*.—45-90°.
*Strength*.—Strong.
*Texture*.—Smooth, glabrous.
*Color*.—Near RHS Violet-Blue 91B.

Fertile flower:
*Bud shape*.—Flattened globular.
*Bud length*.—3-4 mm.
*Bud diameter*.—3-4 mm.
*Bud color*.—Begins RHS Greyed-Green 193 and 193C, turns Violet 86A and 86B.
*Flower aspect*.—Upright facing.
*Flower shape*.—Rotate.
*Flower diameter*.—1.0 cm.
*Flower depth/length*.—1.0 cm.
*Persistence*.—Self-cleaning.
*Longevity on plant*.—About 4 weeks.

Fertile flower petals:
*Arrangement*.—Single whorl.
*Quantity*.—Typically 5. Occasionally 6 or 7.
*Length of petal*.—3.0 mm.
*Width of petal*.—1.0 to 1.5 mm.
*Apex*.—Acute to acuminate.
*Shape of petal*.—Elliptic to ovate.
*Petal margin*.—Entire.
*Petal base*.—Truncate.
*Petal texture*.—Smooth, glabrous, upper and under side.
*Color*.—Upper surface at first opening: Near RHS Violet 84B and 84C. Under surface at first opening: Near RHS Violet 84B and 84C. Upper surface at maturity: Near RHS Violet-Blue 92A and 92B. Under surface at maturity: Near RHS Violet-Blue 92A and 92B.

Fertile flower sepal: None observed.

Fertile flower pedicel:
*Angle*.—Range of 0-90° from attachment.
*Strength*.—Strong.
*Length*.—Average range between 3.0 to 5.0 mm.
*Width*.—1.0 mm.
*Texture*.—Smooth, glabrous.
*Color*.—Near RHS Violet-Blue 95C.

REPRODUCTIVE ORGANS

Sterile flowers: Reduced, mal-formed infertile anthers observed. Less than 1 mm. Colored near RHS Violet-Blue 92C. Reduced, infertile gynoecium observed. Individual parts indistinguishable, less than 2 mm long and 1 mm wide. Colored near RHS Violet-Blue 92D.

Fertile flowers:

Stamens:
*Number*.—Most commonly 10.
*Filament length*.—3 mm.
*Filament color*.—Near RHS Violet-blue 96C.

Anthers:
*Shape*.—Rounded, 2-lobed.
*Length*.—0.8 mm.
*Color*.—Near RHS Yellow-White 158B.
*Pollen color*.—Near RHS Yellow-White 158B.
*Pollen amount*.—Abundant.

Pistil:
*Number*.—4.
*Length*.—0.5-1 mm.
*Style*.—Length: About 1 mm. Color: Near RHS Violet-Blue 96C.
*Stigma*.—Shape: Capitate to discoid. Color: Near RHS Violet-Blue 96C.

OTHER CHARACTERISTICS

Seeds and fruits: Moderate quantity of small dust like seeds. Less than 1 mm wide and 1 mm long. Colored near RHS Greyed-Brown N199A.

Disease/pest resistance: Neither resistance nor susceptibility to normal diseases and pests of *Hydrangea* have been observed.

Temperature tolerance: USDA Zones 4 to 9.

What is claimed is:

1. A new and distinct cultivar of *Hydrangea* plant named 'ILVOCLOU' as herein illustrated and described.

* * * * *